United States Patent [19]
Palcic et al.

[11] Patent Number: 5,827,190
[45] Date of Patent: Oct. 27, 1998

[54] ENDOSCOPE HAVING AN INTEGRATED CCD SENSOR

[75] Inventors: Branko Palcic; Calum MacAulay; Stephen Lam; Bruno Jaggi, all of Vancouver, Canada

[73] Assignee: Xillix Technologies Corp., Richmond, Canada

[21] Appl. No.: 699,607

[22] Filed: Aug. 19, 1996

Related U.S. Application Data

[62] Division of Ser. No. 218,662, Mar. 28, 1994, Pat. No. 5,590,660.

[51] Int. Cl.$^6$ ............................................. H61B 6/00
[52] U.S. Cl. ................................. 600/476; 600/109
[58] Field of Search .......................... 128/664, 665, 128/633; 600/181, 178, 118, 109, 160, 473, 476, 310

[56] References Cited

U.S. PATENT DOCUMENTS

| | | |
|---|---|---|
| 4,473,841 | 9/1984 | Murakoshi et al. . |
| 4,541,438 | 9/1985 | Parker et al. ............... 128/664 |
| 4,556,057 | 12/1985 | Hiruma et al. . |

(List continued on next page.)

FOREIGN PATENT DOCUMENTS

| | | |
|---|---|---|
| 0215772 | 3/1987 | European Pat. Off. . |
| 0 512 965 A1 | 11/1992 | European Pat. Off. . |
| 2-22331 | of 1983 | Japan . |
| 59-139237 | 8/1984 | Japan . |
| 2203831 | 10/1988 | United Kingdom . |
| 86/02730 | 5/1986 | WIPO . |
| 90/12536 | 11/1990 | WIPO . |

OTHER PUBLICATIONS

Alfano et al., "Fluorescence Spectra from Cancerous and Normal Human Breast and Lung Tissues," *IEEE Journal of Quantum Electronics*, QE–23(10): 1806–1811 (1987).

Andersson–Engels et al., "Tissue Diagnostics Using Laser–Induced Fluorescence," Ber. Bunsenges, *Phys. Chem.*, 93: 335–342 (1989).

Coffey et al, "Evaluation of Visual Acuity During laser Photoradiation Therapy of Cancer," *Lasers in Surgery and Medicine*, 4: 65–71 (1984).

Cothren et al., "Gastrointestinal Tissue Diagnosis by Laser–Induced Fluorescence Spectroscopy at Endoscopy," *Gastrointestinal Endoscopy*, 36(2): 105–111 (1990).

Dougherty et al., "Cutaneous Phototoxic Occurrences in Patients Receiving Photofrin," *Lasers in Surgery and Medicine*, 10: 485–488 (1990).

(List continued on next page.)

*Primary Examiner*—Brian Casler
*Attorney, Agent, or Firm*—Christensen, O'Connor, Johnson & Kindness PLLC

[57] ABSTRACT

An apparatus and method for imaging diseases in tissue are presented. The apparatus employs a light source for producing excitation light to excite the tissue to generate autofluorescence light and for producing illumination light to generate reflected and back scattered light (remittance light) from the tissue. Optical sensors are used to receive the autofluorescence light and the remittance light to collect an autofluorescence light image and a remittance light image. A filter acts to integrate the autofluorescence image over a range of wavelengths in which the autofluorescence intensity for normal tissue is substantially different from the autofluorescence intensity for diseased tissue to establish an integrated autofluorescence image of the tissue. The remittance light image provides a background image to normalize the autofluorescence image to account for image non-uniformity due to changes in distance, angle and illumination intensity. A monitor displays the integrated autofluorescence image and the remittance light image to produce a normalized image in which diseased tissue is distinguishable from normal tissue. The optical sensor can be installed adjacent the end of an endoscope probe inserted into a body cavity. A method for imaging diseased tissue using an integrated fluorescence image and a normalizing remittance image is also disclosed.

21 Claims, 8 Drawing Sheets

U.S. PATENT DOCUMENTS

| | | |
|---|---|---|
| 4,718,417 | 1/1988 | Kittrell et al. . |
| 4,719,508 | 1/1988 | Sasaki et al. . |
| 4,768,513 | 9/1988 | Suzuki . |
| 4,773,097 | 9/1988 | Suzaki et al. . |
| 4,774,568 | 9/1988 | Matsuo . |
| 4,786,813 | 11/1988 | Svanberg et al. . |
| 4,805,597 | 2/1989 | Iwakoshi . |
| 4,821,117 | 4/1989 | Sekiguchi . |
| 4,827,908 | 5/1989 | Matsuo . |
| 4,852,579 | 8/1989 | Gilstad et al. . |
| 4,858,001 | 8/1989 | Milbank et al. . |
| 4,860,731 | 8/1989 | Matsuura . |
| 4,867,137 | 9/1989 | Takahashi . |
| 4,868,647 | 9/1989 | Uehara et al. . |
| 4,878,113 | 10/1989 | Nakamura . |
| 4,900,934 | 2/1990 | Peeters et al. . |
| 4,913,142 | 4/1990 | Kittrell et al. . |
| 4,930,516 | 6/1990 | Alfano et al. . |
| 4,938,205 | 7/1990 | Nudelman . |
| 4,957,114 | 9/1990 | Zeng et al. . |
| 4,981,138 | 1/1991 | Deckelbaum et al. ................. 128/665 |
| 4,993,404 | 2/1991 | Lane . |
| 4,998,972 | 3/1991 | Chin et al. . |
| 5,003,977 | 4/1991 | Suzuki et al. . |
| 5,042,494 | 8/1991 | Alfano . |
| 5,071,417 | 12/1991 | Sinofsky . |
| 5,078,150 | 1/1992 | Hara et al. . |
| 5,090,400 | 2/1992 | Saito . |
| 5,091,652 | 2/1992 | Mathies et al. . |
| 5,115,137 | 5/1992 | Andersson-Engels et al. . |
| 5,125,404 | 6/1992 | Kittrell et al. . |
| 5,131,398 | 7/1992 | Alfano et al. . |
| 5,196,928 | 3/1993 | Karasawa et al. . |
| 5,255,087 | 10/1993 | Nakamura et al. ..................... 600/109 |
| 5,318,023 | 6/1994 | Vari et al. . |
| 5,318,024 | 6/1994 | Kittrell et al. . |
| 5,377,676 | 1/1995 | Vari et al. . |
| 5,408,996 | 4/1995 | Salb ....................................... 128/665 |
| 5,408,998 | 4/1995 | Mersch ................................... 128/633 |
| 5,421,337 | 6/1995 | Richards-Kortum et al. . |
| 5,421,339 | 6/1995 | Ramanujam et al. . |
| 5,442,438 | 8/1995 | Batchelder et al. ..................... 356/301 |
| 5,507,287 | 4/1996 | Palcic et al. ............................ 600/310 |
| 5,590,660 | 1/1997 | MacAulay et al. ..................... 600/476 |
| 5,697,373 | 12/1997 | Richards-Kortum et al. .......... 600/476 |

OTHER PUBLICATIONS

Hirano et al., "Photodynamic Cancer Diagnosis and Treatment System Consisting of Pulse Lasers and an Endoscopic Spectro–Image Analyzer," *Lasers in Life Sciences,* 3(1): 1–18 (1989).

Hung et al., "Autofluorescence of Normal and Malignant Bronchial Tissue," *Lasers in Surgery and Medicine,* 11: 99–105 (1991).

Ikeda, "New Bronchial TV Endoscopy System," Elsevier Science Publishers B.V. Biomedical Press (1988).

Kapadia et al., "Laser–Induced Fluorescence Spectroscopy of Human Colonic Mucosa," *Gastroenterology,* 99: 150–157 (1990).

Kato et al., "Early Detection of Lung Cancer by Means of Hematoporphyrin Derivative Fluorescence and Laser Photoradiation," *Clinics in Chest Medicine,* 6(2): 237–253 (1985).

Kato et al., "Photodynamic Diagnosis in Respiratory Tract Malignancy Using an Excimer Dye Laser System," *Journal of Photochemistry and Photobiology,* B:Biology, 6: 189–196 (1990).

Lam et al., "Fluorescence Detection," *Advances in the Diagnosis and Therapy of Lung Cancer,* Blackwell Scientific Publication Inc., In Press: 1–32 (1991).

Lam et al., "Detection of Lung Cancer by Ratio Fluorometry With and Without Photofrin II," *SPIE* 1201: 561–568 (1990).

Lam et al., "Detection of Early Lung Cancer Using Low Dose Photofrin II," *Chest,* 97: 333–337 (1990).

Lam et al., "Mechanism of Detection of Early Lung Cancer by Ratio Fluorometry," *Lasers in the Life Sciences,* 4(2)L 67–73 (1991).

Mullooly et al., "Dihematoporphyrin Ether–Induced Photosensitivity in Laryngeal Papilloma Patients," *Lasers in Surgery and Medicine,* 10: 349–356 (1990).

Palcic et al., "Development of a Lung Imaging Fluorescence Endoscope," *Proceedings of the 12th Annual Int'l Conference of the IEEE Engineering in Medicine and Biology Society,* 12(1): 196–197(1990).

Palcic et al., "The Importance of Image Quality for Computing Texture Features in Biomedical Specimens," *SPIE,* 1205: 155–162 (1990).

Palcic et al. "Lung Imaging Fluorescence Endoscope: A Device for Detection of Occult Lung Cancer," *Medical Design and Material,* pp. 1–10 (1991).

Palcic et al., "Lung Imaging Fluorescence Endoscope: Development and Experimental Prototype," *SPIE,* 1448: 113–117 (1991).

Palcic et al., "Detection and Localization of Early Lung Cancer by Imaging Techniques," *Chest,* 99: 742–743 (1991).

Peak et al., "DNA–to–Protein Crosslinks and Backbone Breaks Caused by FAR–and Near–Ultraviolet and Visible Light Radiations in Mammalian Cells," *Mechanism of DNA Damage and Repair,* pp. 193–202 (1986).

Profio et al., "Digital Background Subtraction for Fluorescence Imaging," *Medical Physics,* 13(5): 717–721 (1986).

Profio et al., "Endoscopic Fluorescence Detection of Early Lung Cancer," *SPIE,* 1426: 44–46 (1991).

Rava et al., "Early Detection of Dysplasia in Colon and Bladder Tissue Using Laser Induced Fluorescence," *SPIE,* 1426: 68–78 (1991).

Razum et al., "Skin Photosensitivity: Duration and Intensity Following Intravenous Hematoporphyrin Derivatives, $H_pD$ and DHE," *Photochemistry and Photobiology,* 46(5): 925–928 (1987).

Richards–Kortum et al., "Spectroscopic Diagnosis of Colonic Dysplasia," *Biochemistry and Photobiology,* 53(6): 777–786 (1991).

Tang et al., "Spectroscopic Differences Between Human Cancer and Normal Lung and Breast Tissues," *Lasers in Surgery and Medicine,* 9: 290–295 (1989).

Wagnieres et al., "Photodetection of Early Cancer by Laser Induced Fluorescence of a Tumor–Selective Dye: Apparatus Design and Realization," *SPIE,* 1203: 43–52 (1990).

Andersson–Engels et al., "Fluorescence Characteristics of Atherosclerotic Plaque and Malignant Tumors," *SPIE,* 1426: 31–43 (1991).

Profio et al., "Laser Fluorescence Bronchoscope for Localization of Occult Lung Tumors," *Medical Physics,* 6: 523–525 (1979).

Profio et al., "Fluorometer for Endoscopic Diagnosis of Tumores," *Medical Physics,* 11(4): 516–520 (1984).

Hayata et al., "Fiberoptic Bronchoscopic Laser Photoradiation for Tumor Localization in Lung Cancer," *Chest,* 82: 10–14 (1982).

Lam et al., "Fluorescence Imaging of Early Lung Cancer," *IEEE Eng. Med. Biology,* 12: (1990).

Montán et al., "Multicolor Imaging and Contrast Enhancement in Cancer–Tumor Localization Using Laser–Induced Fluorescence in Hematoporphyrin–derivative–bearing Tissue," *Optics Letters,* 10(2): 56–58 (1985).

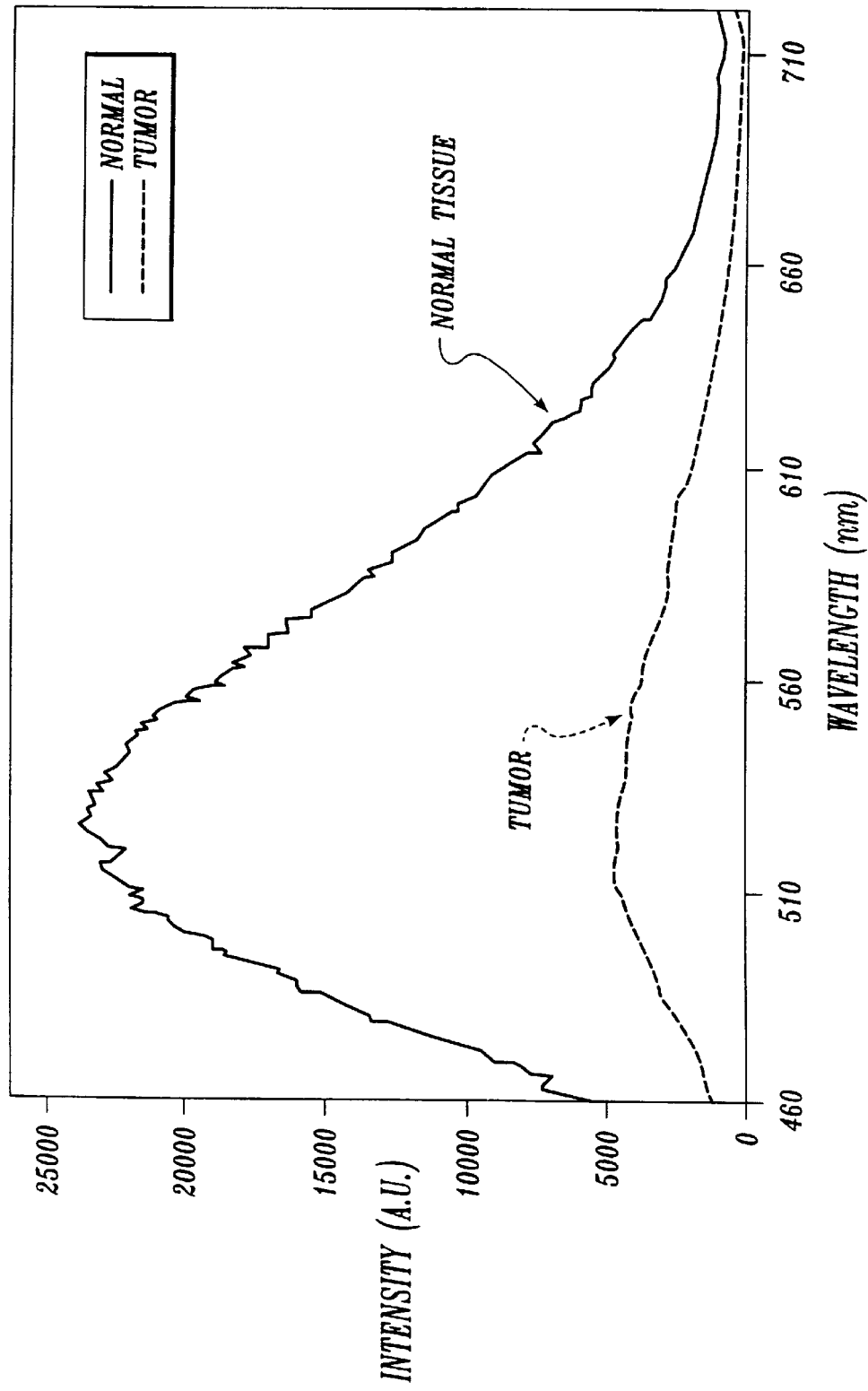

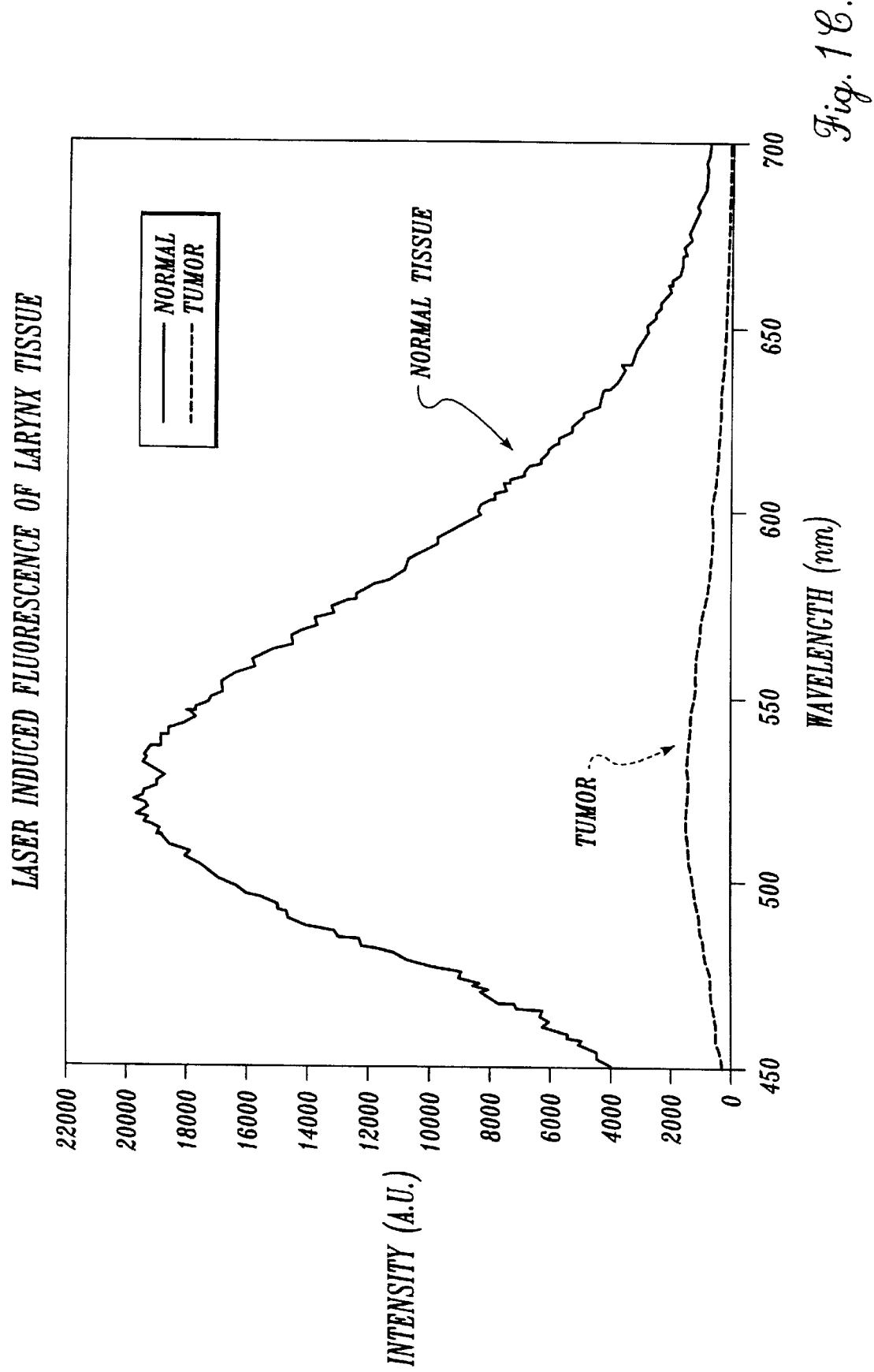

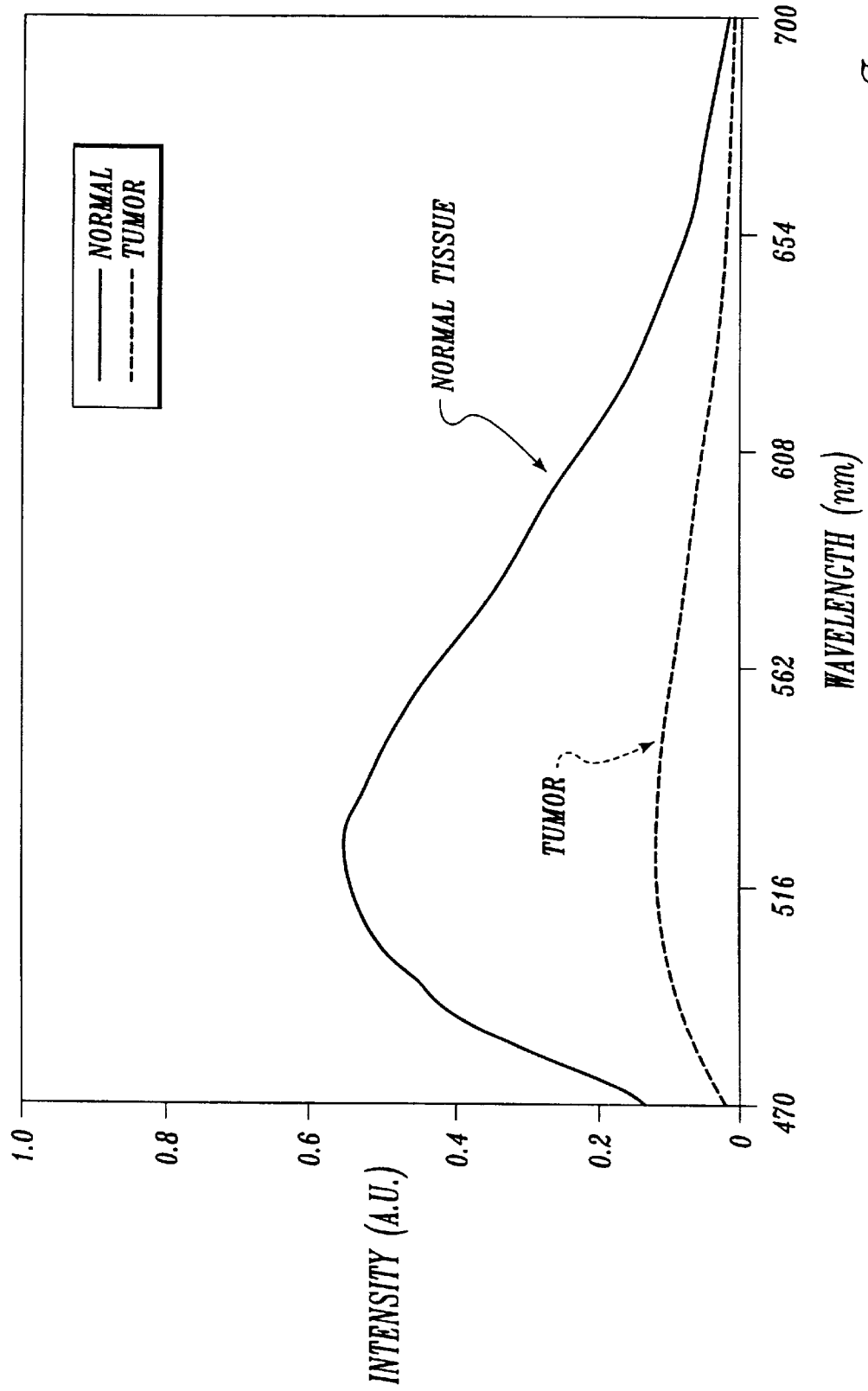

ENDOSCOPE HAVING AN INTEGRATED CCD SENSOR

This is a divisional of the prior application Ser. No. 08/218,662, filed on Mar. 28, 1996, U.S. Pat. No. 5,590,660 the benefit of the filing date of which are hereby claimed under 35 U.S.C. § 120.

FIELD OF THE INVENTION

This invention relates to an endoscope apparatus and method for viewing tissue within the body that uses autofluorescence of the tissue to detect and delineate diseased tissue.

BACKGROUND OF THE INVENTION

Fluorescence endoscopy involves introducing excitation light into the body and collecting the emitted fluorescence light by means of a probe that is inserted into the body to the location of interest. The probe comprises a lens fitted onto a coherent bundle of glass fibres which brings the fluorescent image out of the body cavity. Alternatively, the probe can be a rigid endoscope without fibre optics. The image brought out of the body is captured by very sensitive photodetectors and further processed in an attempt to delineate diseased tissue on the basis that diseased tissue has a different fluorescence intensity than normal tissue. This process loses significant amounts of light due to the image transfer through the optical fibres and a great deal of effort in developing new fluorescence endoscope systems is directed toward new ways of acquiring, enhancing and analyzing the very faint fluorescence images to extract as much information as possible.

An example of an endoscope system that relies on this foregoing general arrangement is disclosed in applicant's co-pending patent application Ser. No. 07/725,283 filed Jul. 3, 1991, now abandoned in favour of continuation application Ser. No. 08/082,019 which is still pending. Other work has been done in this field that attempts to exploit the different fluorescence spectra of diseased and healthy tissue. U.S. Pat. Nos. 5,131,398 to Alfano, U.S. Pat. No. 4,930,516 to Alfano, and U.S. Pat. No. 4,786,813 to Svanberg et al. disclose various equipment and methods that acquire and process fluorescence images in an attempt to detect and delineate diseased tissue.

At present, many fluorescence endoscopy systems rely on drugs with strong fluorescence signals as well as very sensitive detectors to detect the emitted fluorescence signals. In applicant's co-pending patent application Ser. No. 08/082,019 filed Jun. 23, 1993, it was shown how tissue autofluorescence alone, without drugs, can be used to detect diseased tissues such as early cancer and others. In this approach, very faint fluorescence signals must be measured at two or more specific wavelengths of emitted fluorescence. To accomplish such a measurement, very sensitive detectors, such as image intensified cameras operating at the limit of their working range must be used. This arrangement works well for detecting some tumours, but care must be taken to correctly adjust the autofluorescence signals to create appropriate images with minimal noise in order to recognize the diseased site under examination. Also, image intensified cameras (or similar detectors) are very large, they employ high voltage circuitry and they cannot be made to fit the end of the endoscope. The fluorescence images must therefore be brought out of tissue cavities through the coherent optical fibers of the endoscope before processing of the images and/or displaying them on a video monitor.

It has been suggested that the acquired fluorescence image of endoscope systems would be of better quality if it could be collected by a sensor at the end of the endoscope probe inserted into the body. The outer diameter of an endoscope probe must be small to allow insertion into various body cavities thereby limiting the size of the sensor that can be mounted at the distal end of the apparatus. As previously stated, fluorescence images are generally extremely faint and it is not possible for these small image sensors to capture the fluorescence images. Theoretically, increasing the excitation irradiance would increase the fluorescence intensity, however, this may also result in unwanted thermal damage or photobleaching of the tissue under examination.

Prior art endoscopes have been developed that permit the image sensor to be located at the tip of the endoscope probe, however, in general, this endoscope equipment is intended for collecting reflected light and is not suitable for reliably capturing faint fluorescence images.

SUMMARY OF THE INVENTION

The present invention seeks to provide an apparatus and method that addresses the problems of the prior art by providing a new system for acquiring fluorescence images that uses integration of autofluorescence intensity over a broad band of wavelengths to acquire a well-defined autofluorescence image that is combined with a remittance light image to create a merged image in which diseased and normal tissue are readily distinguishable. The remittance light image is used to normalize the autofluorescence image to account for image non-uniformity due to changes in distance, angle and illumination intensity.

The present invention exploits applicant's discovery that in vivo tissue autofluorescence of diseased tissue is greatly reduced through a significant range of the visible light spectrum (from approximately 500 nm to approximately 700 nm). To exploit this natural phenomenon, the present novel system was designed and developed to use the integrated fluorescence over this large spectral range (500 nm −700 nm) and display the fluorescence image along with a remittance light image such that, to the observer, normal tissue appears in a different colour from diseased tissue. In the present application, remittance light refers to reflected and back scattered light. Fluorescence signal intensity is dependent on such factors as the excitation light intensity, the proximity of the excitation light source to the tissue, and the angle of incidence of the excitation light to the tissue. To normalize for these factors, prior art systems have used two (or more) different narrow wavelength bands of fluorescence, one of which is used for normalization purposes. This requires a precondition that the difference in the tissue autofluorescence intensity between the two wavelengths must not be the same as otherwise normalization of an image could not be achieved.

In the apparatus and method of the present invention, two wavelengths of light for imaging a tissue site can be used. Preferably, blue light is used as excitation light to induce tissue autofluorescence and red/near-infrared light (approx. 700 nm) is used to produce a remittance light image. Alternatively, a single wavelength of light can be used as excitation light and a remittance light image can be collected from the remitted excitation light. The integrated autofluorescence image and the remittance light image are combined and displayed in a form to allow the observer to intuitively adjust for the excitation light intensity variations.

Accordingly, in a first embodiment, the present invention provides apparatus for imaging diseases in tissue comprising:

a light source for producing excitation light to excite the tissue to generate autofluorescence light and for producing illumination light to generate remittance light from the tissue;

optical means for receiving the autofluorescence light and the remittance light to collect an autofluorescence light image and a remittance light image;

means for integrating the autofluorescence image over a range of wavelengths in which the autofluorescence intensity for normal tissue is substantially different from the autofluorescence intensity for diseased tissue to establish an integrated autofluorescence image of the tissue; and display means for displaying the integrated autofluorescence image and the remittance light image to produce a normalized image in which diseased tissue is distinguishable from normal tissue.

In a further aspect the present invention provides, a method for imaging diseases in tissue comprising:

exciting the tissue to autofluoresce with excitation light to generate autofluorescence light;

illuminating the tissue with illumination light to generate remittance light;

detecting the autofluorescence light;

integrating the intensity of autofluorescence light over a range of wavelengths in which the autofluorescence intensity for normal tissue is substantially different from the autofluorescence intensity for diseased tissue to establish an integrated autofluorescence image of the tissue;

detecting the remittance light to establish a remittance light image; and combining the integrated autofluorescence image and the remittance light image to produce a normalized image in which diseased tissue is distinguishable from normal tissue.

In a further embodiment, the present invention provides a fluorescence endoscope apparatus having an image sensing device that is positioned at the end of a probe comprised of light guides. The probe is introduced into the body thereby eliminating the problem of fluorescence image degradation due to light loss while travelling through the collecting light guides. The image sensing device can be positioned adjacent to the tissue surface being examined so that there is little loss of light.

To solve the problem of reliable and accurate acquisition of a faint fluorescence image the apparatus of the present invention employs an image sensing device such as a CCD (or equivalent such as CID) array having a sensitivity that can be varied. A preferred way to achieve increased sensitivity of the CCD array is to combine individual pixel sensing elements to create larger to very large sensing units. Individual sensing elements can be combined together into 2×2, 4×4, 8×8, 16×16 or even larger groups creating new larger sensing units, particularly if CCDs are used with 100% fill factor and high quantum efficiency. With special noise suppressing circuitry very sensitive detectors can be made with very low noise, i.e. very high signal-to-noise ratio (SNR), well within parameters to detect the low fluorescence emitted by tissues.

Accordingly, in the further embodiment the present invention provides an endoscope apparatus for imaging a disease site within a body comprising:

a probe having an inner end to be located within the body near the disease site and an outer end to extend outside the body;

a light source at the outer end of the probe for generating light that includes excitation light to induce tissue fluorescence, the probe conveying the excitation light from the outer end to the inner end to illuminate the disease site and cause the tissue to fluoresce;

image sensing means at the inner end of the probe to detect tissue fluorescence, the image sensing means having a light sensitivity that can be increased to acquire low resolution images at low fluorescent light intensities and decreased to acquire high resolution images at other light intensities;

filtering means at the inner end of the probe for filtering out the excitation light; and display means connected to the outer end of the probe for displaying the filtered image detected by the image sensing means in such a manner as to delineate diseased and normal tissue due to diseased tissue having diminished fluorescence in comparison to normal tissue.

BRIEF DESCRIPTION OF THE DRAWINGS

Aspects of the present invention are illustrated, merely by way of example, in the accompanying drawings in which:

FIGS. 1b to 1d are graphs showing actual autofluorescence curves for tissue samples;

DESCRIPTION OF THE PREFERRED EMBODIMENTS

Figure 1A:
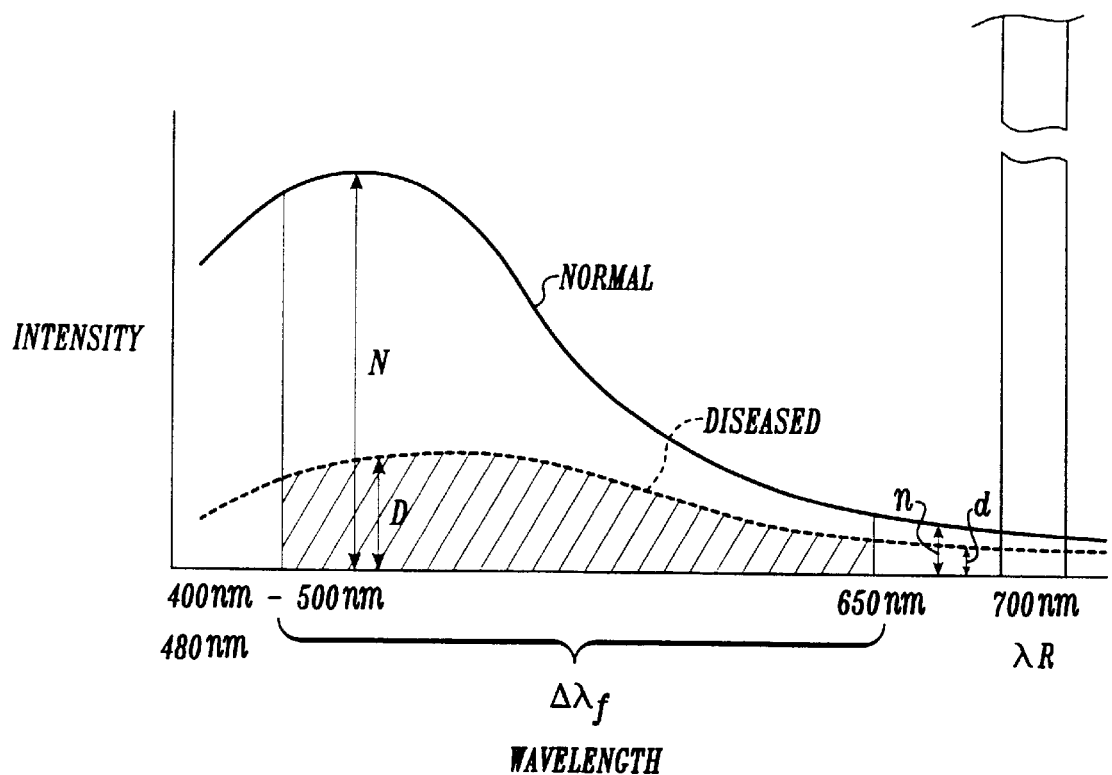
FIG. 1a is a graph showing a typical autofluorescence curve of light intensity over a range of wavelengths for in vivo tissue exposed to excitation light.

FIG. 1a shows a typical graph of the autofluorescence response spectrum of tissue in vivo when exposed to blue excitation light (400 nm –450 nm). Applicant has discovered that autofluorescence of diseased tissue in vivo is greatly reduced as compared to normal tissue through the entire range of visible light (from approximately 500 nm to approximately 700 nm). FIGS. 1b–1d are examples of actual autofluorescence curves for tissue illuminated by blue excitation light. In FIG. 1b, the autofluorescence spectrum for bronchial tissue is shown. Note that the autofluorescence intensity for normal tissue and tumorous tissue both peak in the green range of the spectrum (approximately 530 nm), however, the peak for tumorous tissue is much lower than the peak for normal tissue. In the region of the spectrum greater than 700 nm, the spectrums for normal and tumor tissue are substantially identical. FIG. 1c shows the autofluorescence spectrum for larynx tissue that is induced to fluoresce using blue laser light. Again, there is a pronounced peak in the green region of the spectrum for normal tissue and a greatly reduced spectrum for tumor tissue having a low peak in the green region. In the region of the spectrum greater than 700 nm, the spectrum is substantially the same for both tissues. In FIG. 1d, the autofluorescence spectrum for nasopharynx tissue is shown having a green region peak for normal tissue and a reduced overall spectrum for diseased tissue. While there are some differences in the autofluorescence spectrum for specific types of tissue, in general, the diseased tissue autofluorescence is significantly reduced in comparison to the normal tissue autofluorescence over a broad spectral band.

Figure 2:
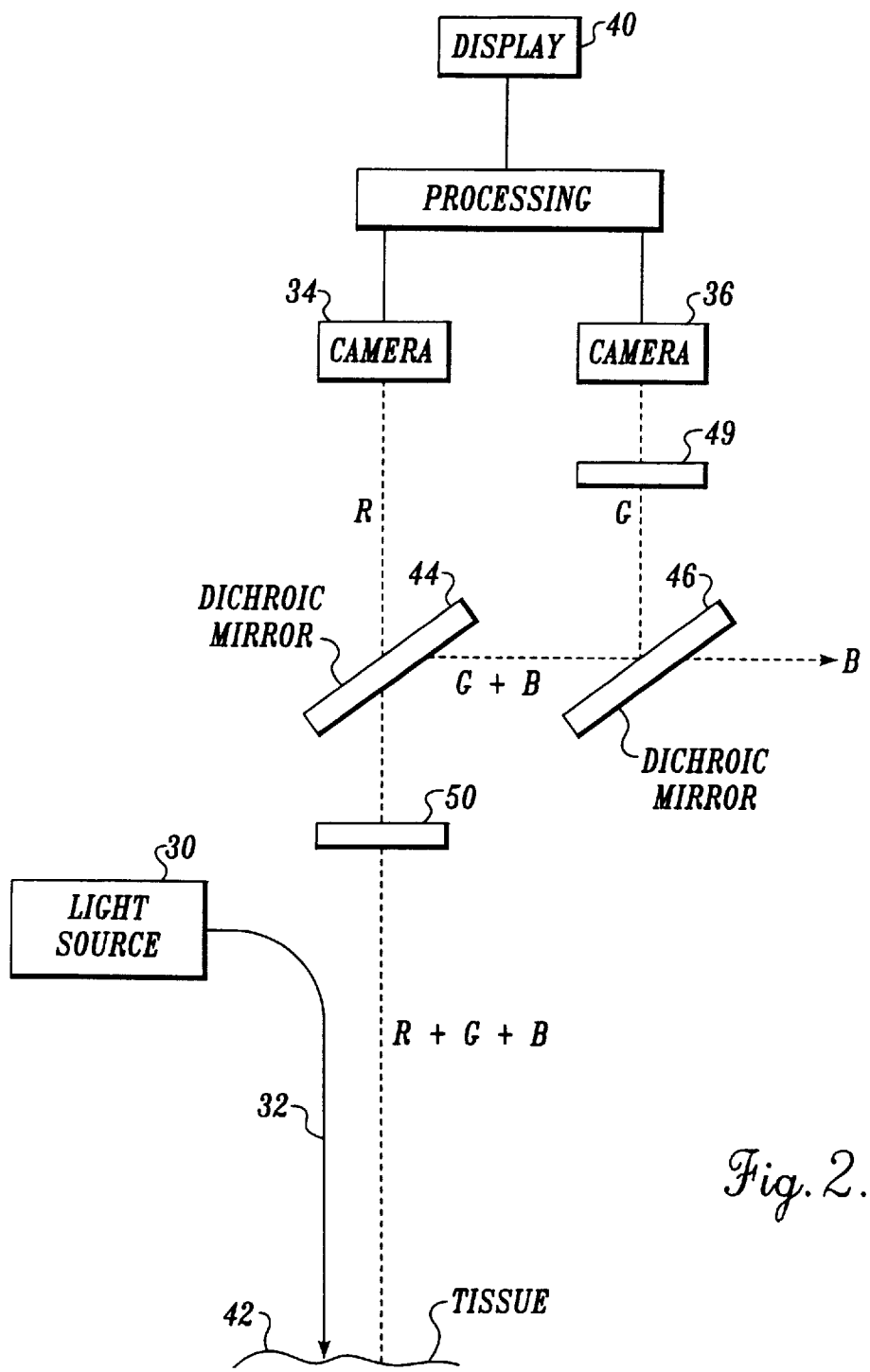
FIG. 2 is a schematic view of a first embodiment of the present invention that employs integrated autofluorescence in which images are acquired simultaneously.

FIG. 2 is a schematic view of apparatus according to a first embodiment that has been developed to exploit the autofluorescence response of the tissue to differentiate between diseased and normal tissue. The apparatus of FIG. 2 employs simultaneous illumination of the tissue with both excitation and illumination light. The apparatus includes a light source 30 for producing excitation light of a first pre-selected wavelength, preferably blue light (400–450 nm), to excite the tissue to autofluoresce. The excited tissue produces a predominantly green autofluorescence light as indicated in FIGS. 1a–1d. Light source 30 also produces non-excitation light of a different wavelength to illuminate the tissue. The non-excitation light is preferably far red to infrared light ($\lambda_R$) including wavelengths greater than 700 nm and is used to produced a remittance light image of the tissue. This non-excitation light-is preferred as it falls outside the relatively broad spectral range of generally green emitted autofluorescence light ($\Delta\lambda_f$) in which autofluorescence intensity for normal tissue is substantially greater than for diseased tissue so as not to interfere with detection of the relatively faint autofluorescence image. Also, far red to infrared light has a low absorption coefficient in most tissue and it has a large scattering coefficient. Additionally, the scattering and absorption coefficients of red to infrared light do not vary much from location to location in most tissues so that red and infrared light is almost uniformly back scattered and reflected from the tissue. This remittance light is therefore relatively uniform in its angular distribution from the tissue and the intensity of light will depend almost entirely on the illumination intensity. Areas that receive less light will backscatter proportionally less in the same manner that autofluorescence emits light proportional to the amount of excitation light. Therefore, red and infrared light can be used to generate an image to correct for non-uniformity in the autofluorescence image that might arise due to changes in the proximity of the excitation light to the tissue, the angle of incidence of the excitation light to the tissue and the intensity of the excitation light. It should be noted that the intensity of remittance light ($\lambda_R$) is much greater than the intensity of the autofluorescence light and a vertical break in the range over which remittance light is collected is provided in FIG. 1a to account for this intensity difference.

The light is delivered to the tissue under examination by a conventional endoscope probe 32 comprising a bundle of optical fibres. Probe 32 also delivers autofluorescence light and remittance light from the tissue to optical means in the form of CCD cameras 34 and 36. CCD camera 36 has associated means for integrating the intensity of the autofluorescence light over a range of wavelengths in which the autofluorescence intensity for normal tissue is substantially different from the autofluorescence intensity for diseased tissue to establish an integrated autofluorescence intensity image of the tissue. The means for integrating the intensity of autofluorescence light preferably comprises a broad band filter 49 to admit autofluorescence light over a broad range of wavelengths. In the case of blue excitation light, the resulting autofluorescence tends to be mainly green light and the intensity is integrated over the range of wavelengths from 500–650 nm designated ($\Delta\lambda_f$) in FIG. 1. In this manner, the need for an image intensifier is obviated as the integrated autofluorescence signal is nearly an order of magnitude stronger compared to the natural autofluorescence intensity in a narrow wave band. In addition, the detected change (DC) between normal and abnormal tissue is approximately 8–10 times, compared to the 1.5–2 times of prior art systems.

Referring to FIG. 1, the DC is defined as:

$$DC_{application} = \frac{N}{D}$$

$$DC_{priorart} = \frac{\frac{N}{D}}{\frac{n}{d}}$$

where
N=the autofluorescence intensity for normal tissue at a wavelength exhibiting the maximum difference between normal and diseased tissue
D=the autofluorescence intensity for diseased tissue at a wavelength exhibiting the maximum difference between normal and diseased tissue
n=the autofluorescence intensity for normal tissue at a wavelength exhibiting the minimum difference between normal and diseased tissue
d=the autofluorescence intensity for diseased tissue at a wavelength exhibiting the minimum difference between normal and diseased tissue Since n/d is usually greater than 1 (in the range of 2 to 5) in prior art systems, the detected change for the apparatus and method of the present invention is generally 2 to 5 times greater than the detected change of the prior art.

The images captured by CCD cameras 34 and 36 are processed and displayed on display means in the form of a monitor 40. The images are preferably processed in an imaging board in a computer. The integrated autofluorescence image captured by camera 36 and the remittance light image captured by camera 34 are combined to produce a normalized image in which diseased tissue is distinguishable from normal tissue. Camera 36 provides a substantially green integrated autofluorescence image that is fed to the green channel of the display and camera 34 provides a substantially red remittance light image to normalize the autofluorescence image that is fed to the red channel of the display to produce a normalized pseudo-colour image. If diseased tissue is present, the intensity of the green autofluorescence image will be reduced over the diseased area while the remittance light image will be substantially unaffected. If tissue is normal, the intensity of the green autofluorescence image will be increased relative to the diseased tissue and the remittance light image will continue to be substantially unaffected. Combining and display of the two images on monitor 40 is arranged such that the relatively constant red remittance light image is used to establish a "underlying" image that accurately displays contours in the tissue and image variations that arise due to the proximity and intensity of the light source to the tissue. The mix of the images is such that normal tissue will appear green and diseased tissue will appear red due to the reduced levels of green autofluorescence in the vicinity of the diseased tissue allowing the red remittance light to predominate.

The apparatus of FIG. 2 is set up such that light source 30 illuminates tissue 42 with the excitation light and illumination light simultaneously and separate CCD cameras 34 and 36 are provided to receive the autofluorescence image and the remittance light image. In this arrangement, light splitting means in the form of dichroic mirrors 44 and 46 are provided to direct the remittance light and the autofluorescence light to the appropriate CCD camera. While traditional 50%, 50% or X%, 100-X% beam splitters may be used, dichroics increase the fluorescence image intensity available to be detected. In FIG. 2, a first dichroic mirror 44 passes the red remittance light (R) to CCD camera 34 and diverts the green autofluorescence light (G) and reflected blue excitation light (B) to second dichroic mirror 46. Second dichroic mirror 46 diverts the green autofluorescence light (G) to CCD camera 36 and passes the blue excitation light (B).

Filter 49 in the path of the autofluorescence light is preferably adjustable to vary the range of wavelengths of autofluorescence light that are received by CCD camera 36. In this manner, the "window" over which autofluorescence is integrated can be varied to fine tune the apparatus to detect different disease conditions in different tissues that tend to exhibit characteristic autofluorescence spectra as illustrated in FIGS. 1b to 1d. Filter 49 can be varied by inserting an appropriate filter into place for the particular tissue and the type of tumour under examination.

In addition, an optional filter means 50 can be included in the light path to prevent blue excitation light from being received by the CCD cameras.

Figure 3:
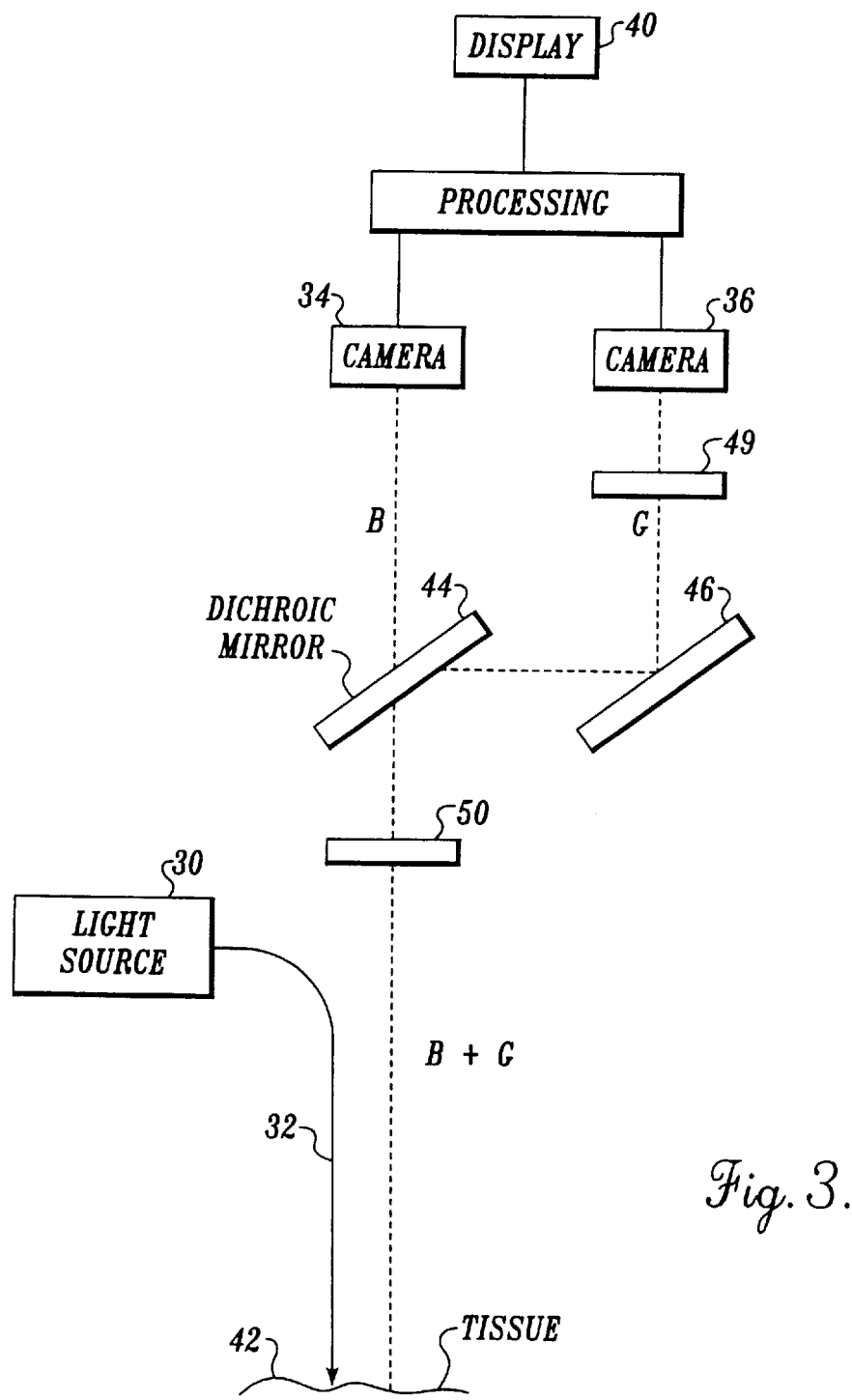
FIG. 3 is a schematic view of a second embodiment of the present invention in which images are acquired sequentially.
Figure 4:
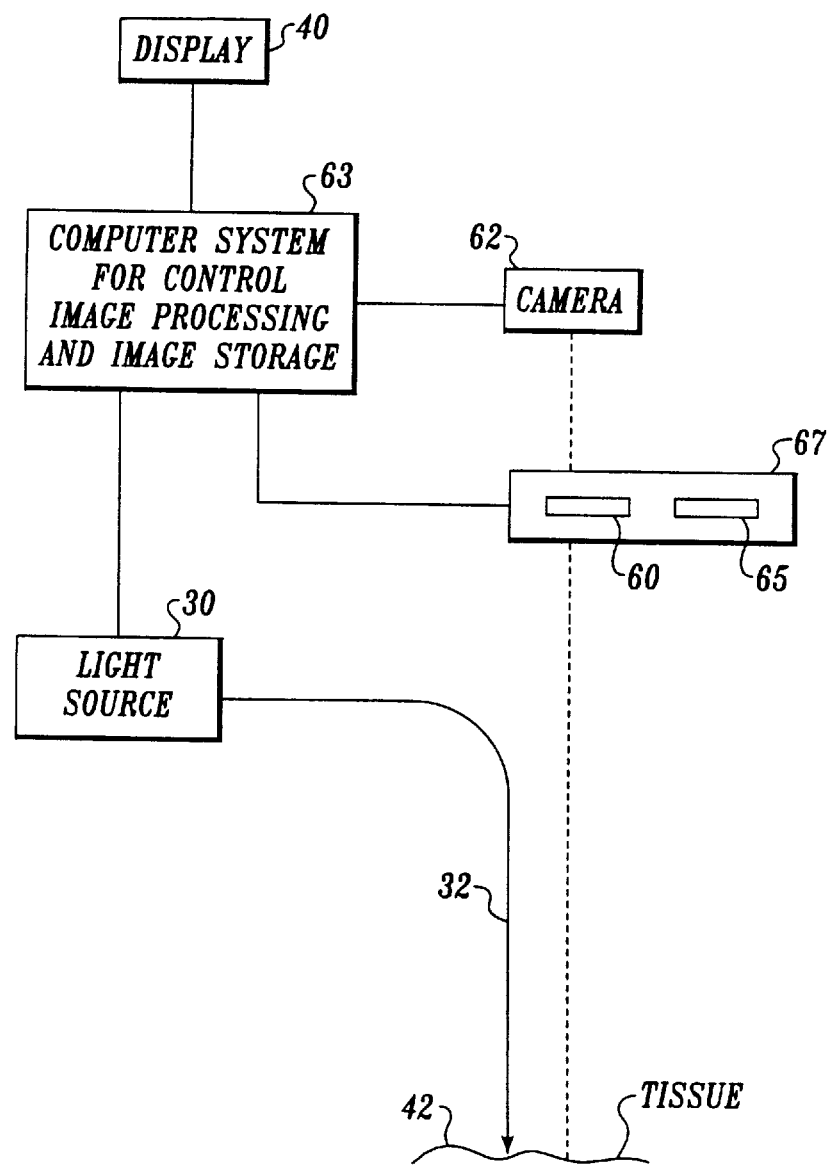
FIG. 4 is a schematic view of a third embodiment of the present invention that uses blue light to produce both the autofluorescence and remittance light images.

While the apparatus of FIG. 2 employs simultaneous illumination of the tissue with both excitation and illumination light, it is also possible to expose the tissue to excitation light and illumination light sequentially. FIG. 3 schematically illustrates imaging apparatus according to a second embodiment of the present invention that illuminates the tissue sequentially over a timing cycle. Light source 30 illuminates tissue 42 through endoscope 32 with excitation light for a first portion of the timing cycle. Autofluorescence light is delivered via endoscope 32 and filter 60 to a single CCD camera 62 in order to capture an integrated autofluorescence image. Filter 60 is positionable before camera 62 to filter out the excitation light and pass broadband autofluorescence light. The captured autofluorescence image is transferred to image processing means and then to image storage means located in a computer 63. Light source 30 then illuminates the tissue with illumination light to generate a remittance light image. If necessary, filter 65 is moved into position to filter the remittance light. Filters 60 and 65 are mounted on a turntable arrangement 67 that is controlled by computer 63. The remittance light image is transferred to the image processing and storage means. The two images collected in the timing cycle are then combined and displayed on monitor 40 in the same manner as previously described using colour to delineate normal and diseased tissue. The cycle is then repeated under the control of computer 63.

The foregoing embodiments of the present invention employ blue excitation light and red illumination light to produce an image that distinguishes normal and diseased tissue. In certain conditions, such as when examining inflamed tissue, the foregoing systems may cause false positive readings. In order to reduce false positive readings for cancer, a third embodiment of the present invention has been developed that employs blue light as both the excitation light and the illumination light. FIG. 3 is a schematic drawing of the apparatus of the third embodiment that is designed to reduce the rate of false positive readings without sacrificing true diseased tissue (true positive) detection rates.

False positive readings arise in inflamed tissue as the increased blood concentration tends to absorb blue excitation light and green autofluorescence light leading to a reduced autofluorescence signal. For prior art autofluorescence systems, the blood absorption causes a large drop in the green autofluorescence image and a slightly less large drop in the red autofluorescence image causing the displayed image to show inflamed tissue differently from normal tissue leading to mistaken identification as diseased tissue. For the blue excitation light, red illumination light imaging of the present invention, the same problems occur. The integrated fluorescence drops and the red remittance image does not change significantly in areas of inflamed tissue, consequently, the displayed image does not appear to show normal tissue and the inflamed area is mistaken for diseased tissue.

In the apparatus of FIG. 3, light source 30 provides blue light for both excitation and illumination light in a manner identical to the embodiment of FIG. 2. Green autofluorescence light (G) and blue remittance light (B) are collected from the tissue site. The combined light is split at dichroic mirror 44. A blue remittance light image is captured by CCD camera 34 and a green autofluorescence image is reflected through integrating filter 49 for capture by CCD camera 49. In this arrangement, the intensity of the detected blue remittance light image tends to drop off almost as much as the green integrated fluorescence image, consequently, the displayed image of inflamed tissue does not differ significantly from normal tissue.

An additional modification of the apparatus of the third embodiment can be used to make the presence of increased blood at a tissue site appear as a recognizable colour on the displayed image that would not be confused with normal or diseased tissue. In the modified apparatus, blue excitation light and red illumination light are used and a blue remittance light image, a red remittance light image and a green integrated autofluorescence image are collected. The red and blue remittance images are captured by camera 34. Camera 34 sends the red remittance image via its red channel and the blue remittance image via its blue channel to display 40. The green integrated autofluorescence image is captured by camera 36 and sent to the green channel of the display. On the display, normal tissue appears white, inflamed tissue has a reddish hue and abnormal tissue has a purplish hue.

Figure 5:
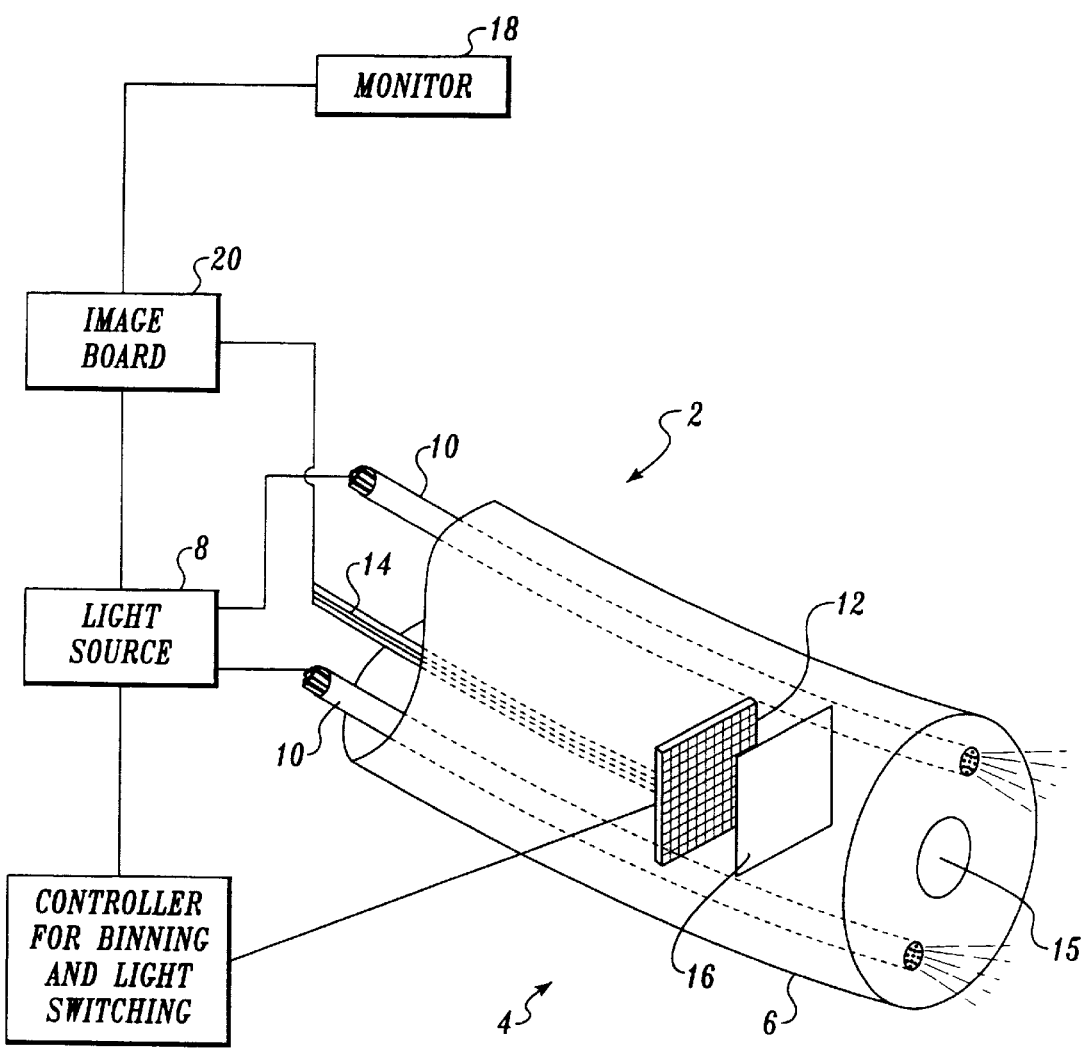
FIG. 5 is a schematic view of a fourth embodiment of the apparatus of the present invention that employs an CCD array positioned at the tip of an endoscopic probe.

The technique of the present invention also allows development of an imaging system that is sufficiently small and compact to be positioned at the end of an endoscope probe. Referring to FIG. 5, there is shown an endoscope system 2 for imaging a disease site within a body according to a fourth embodiment of the present invention. The apparatus includes a probe 4 having an inner end 6 that is insertable into a body to be located near the disease site. The outer end of probe 4 remains outside the body for connection to a light source 8 for generating light and display means in the form of a colour monitor 18 for displaying the image collected by probe 4.

Light source 8 generates light at the outer end of the probe that includes excitation light to induce tissue fluorescence. The probe is comprised of a bundle of optical fibres 10 that convey the light of source 8 from the outer end to inner end 6 to illuminate the disease site. At inner end 6, there is provided image sensing means, preferably in the form of CCD sensor 12 to detect and collect an image of the diseased site using remittance light and emitted fluorescent light. CCD array 12 communicates with the outer end of probe 4 via electrical connection 14 that extends through probe 4.

Preferably, inner end 6 is provided with a lens 15 to focus light on CCD sensor 12. Filtering means in the form of a filter module 16 is positioned before CCD sensor 12. Filter module 16 can be fixed in place or removable remotely. Alternatively, the filtering means can be a coating applied directly to surface of CCD sensor 12. In a still further arrangement, filter module 16 can be associated with lens 15. The filter module 16 acts to exclude excitation light and pass light of other wavelengths to the image sensing means, particularly emitted fluorescent light.

The image collected by CCD sensor 12 is transmitted via line 14 to the outer end of probe 4 for viewing on display means in the form of a colour monitor 18. The image displayed on monitor 18 delineates diseased and normal tissue for viewing by the endoscope operator.

The endoscope apparatus of the fourth embodiment is able to collect the faint fluorescence images that provide information necessary for delineating diseased an normal tissue by virtue of the fact that CCD sensor 12 is provided with a light sensitivity that can be increased to acquire low resolution images at low fluorescent light intensities and decreased to acquire high resolution images at other light intensities.

The light sensitivity of CCD sensor 12 is adjusted by binning the pixels of the sensor array. Binning the pixels decreases spatial resolution. For example, a CCD sensor comprised of 250×250, (i.e. 62,500 active pixels) if binned to form 8×8 pixels per each new sensor unit would yield an effective CCD of approximately 30×30 pixels (each pixel being 64 times larger than the original pixels) providing a very low resolution image. However, dynamic binning can solve the problem of the low spatial resolution as will be described below.

In operation, light source 8 can provide a broad spectral band of excitation light ranging in wavelength between 400–480 nm (broad band blue light). Such an excitation light tends to generate a strong fluorescence response in most tissues such as the lungs, the esophagus, the colon, the bladder and the skin. The peak fluorescence is in the green region at approximately 510 nm and it has been shown that the fluorescence signal is greatly diminished or virtually disappears in abnormal tissue due to early cancer or dysplasia. Alternatively, the excitation light can be in a narrow spectral band of blue or violet light.

The blue excitation light of light source 8 is conveyed to inner probe end 6 to illuminate an internal disease site to induce maximum tissue fluorescence particularly in the green and longer wavelengths. Scattered/reflected excitation light and fluorescence light are focused by lens 15 on CCD sensor through filter module 16. Filter module 16 is selected to filter out the blue band excitation light such that only the fluorescence green and longer wavelengths (e.g. greater than 480 nm) are collected by the CCD sensor. Since abnormal tissue has greatly diminished (or a lack of) fluorescence particulary in the green region, the abnormal tissue will be detected as a darker area on the image captured by the CCD sensor. The darker abnormal regions of tissue will be readily apparent on display monitor 18. The light sensitivity of the CCD sensor can be increased by binning to acquire low resolution images at low fluorescent light intensities. While the images are of reduced resolution, they are generally sufficiently detailed to accurately determine the extent and location of the diseased tissue.

The arrangement of the fourth embodiment of the present invention reduces the complexity of the apparatus as there is generally no longer the need for an image intensifier to enhance the image collected by the CCD sensor since the sensor is located immediately adjacent the image site and the binning of the CCD sensor permits acquisition of very faint fluorescence images albeit at reduced resolution.

In a variation of the fourth embodiment, high resolution non-fluorescence images and low resolution fluorescence images of the disease site can be acquired sequentially and combined for display on monitor 18. In this variation, the endoscope apparatus is identical to the fourth embodiment except light source 8 is modified to sequentially illuminate the disease site with two or more wavelengths of light over a timing cycle. One wavelength is a fluorescence excitation light that is on for the majority of the timing cycle and the other wavelength is a non-excitation light that is on for a short period of the timing cycle. This arrangement requires means to increase the image sensing means sensitivity to acquire a low resolution fluorescence image during illumination by the fluorescence excitation light and decrease the image sensing means sensitivity to acquire a high resolution image during illumination by the non-excitation light. This arrangement also requires image processing means for storing sequential images captured by the image sensing means and combining the images for display as a pseudo-colour image on the display means.

Preferably, the endoscope apparatus of the present embodiment is operated in the following manner:

Light source 8 sequentially illuminates the disease site briefly through probe 6 with red non-excitation light and blue fluorescence excitation light over a single cycle of 30 msec which is consistent with video display rates. The scattered and/or reflected red light is passed through filter module 16 in front of the CCD sensor 12. The red light is sufficiently intense that CCD sensor 12 does not have to be binned and an image of the site at high resolution is captured by the sensor. The illumination with red light is of short duration (e.g. 5 msec pulse) and the image is stored in a buffer of the image processing means comprising an imaging board 20. The blue light is of much longer duration (e.g. 25 msec) to collect sufficient fluorescence light generated by the blue light. In addition, the CCD is now binned if necessary to detect and capture the fluorescence image of the site at reduced resolution. Filter module 16 excludes the blue excitation light and permits passage of green and longer wavelengths. The captured fluorescence image is fed into another buffer of the imaging board. A pseudo image is then formed by the imaging board for display on RGB monitor 18. The pseudo image is a composite image that includes a very high resolution colour image (generated using the red light) superimposed on a green to dark green lower resolution image (generated using the blue light). In the composite image, normal tissue will be green and diseased or abnormal tissue will show up as red or pink areas. This combination of fluorescence and reflectance imaging has the additional advantage of compensating for changes in fluorescence intensity due to variation in the distance and angle between the probe and the surface of the body cavity.

Although the present invention has been described in some detail by way of example for purposes of clarity and understanding, it will be apparent that certain changes and modifications may be practised within the scope of the appended claims.

We claim:

1. Endoscope apparatus for imaging tissue within a body comprising:

a probe having an inner end to be located within the body near the tissue under examination and an outer end to extend outside the body;

a light source at the outer end of the probe for generating light that includes excitation light to cause the tissue to produce autofluorescence light having an intensity that is different for healthy tissue than for diseased tissue, the probe conveying the excitation light from the outer end to the inner end to illuminate the tissue;

image sensing means at the inner end of the probe to detect the autofluorescence light and produce an image of the tissue under examination on a single channel, the image sensing means having a light sensitivity that can be increased to produce low resolution images at low autofluorescence light intensities and decreased to produce higher resolution images at other light intensities;

a filter disposed between the imaging sensing means and the tissue under for filtering out the excitation light from the light that reaches the image sensing means; and a display connected to receive a filtered image produced by the image sensing means and for displaying the filtered image in such a manner as to delineate diseased and normal tissue.

2. Endoscope apparatus as claimed in claim 1 in which the image sensing means is a CCD array.

3. Endoscope apparatus as claimed in claim 2, further comprising a controller coupled to the CCD array for increasing the light sensitivity of the CCD array by binning pixels of the CCD array.

4. Endoscope apparatus as claimed in claim 2 in which the filter comprises a coating on the CCD array.

5. Endoscope apparatus as claimed in claim 1 including a lens at the inner end of the probe to focus the autofluorescence light on the image sensing means.

6. Endoscope apparatus as claimed in claim 1 in which the light source generates excitation light in a broad spectral band ranging from 400 nm to 480 nm.

7. Endoscope apparatus as claimed in claim 1 in which the light source generates excitation light in a narrow spectral band of blue or violet light.

8. Endoscope apparatus as claimed in claim 1 in which the filter comprises a long pass blue filter.

9. Endoscope apparatus as claimed in claim 1 in which the filter excludes excitation light and passes light of other wavelengths to the image sensing means.

10. Endoscope apparatus as claimed in claim 9 in which the filtering means excludes blue excitation light and passes green and longer wavelength light.

11. Endoscope apparatus as claimed in claim 9 in which the light source sequentially illuminates the tissue under examination with two or more wavelength bands of light over a timing cycle, one wavelength band being the excitation light that causes the tissue under examination to produce autofluorescence light and the other wavelength band being non-excitation light that is reflected off the tissue under examination and passed through the filter, wherein the sensitivity of the image sensing means is increased to produce a low resolution autofluorescence image of the tissue under examination during illumination by the excitation light and decreased to produce a higher resolution reflectance image of the tissue under examination during illumination by the non-excitation light.

12. Endoscope apparatus as claimed in claim 11 in which the excitation light is on for a portion of the timing cycle that is greater than a portion of the timing cycle during which the non-excitation light is on.

13. Endoscope apparatus as claimed in claim 11 including image processing means for storing sequential autofluorescence and reflectance images produced by the image sensing means and combining the fluorescence and reflectance images for simultaneous display as a pseudo-colour image on the display.

14. Endoscope apparatus as claimed in claim 11 in which the non-excitation light is substantially red and the excitation light is substantially blue.

15. A method of imaging tissue within a body using autofluorescence light, comprising:

inserting a probe of the type having an image sensing device disposed at a distal end of the probe;

illuminating the tissue under examination with an excitation light that causes the tissue to produce autofluorescence light having an intensity that differs for healthy tissue than for diseased tissue;

storing a first image created by the image sensing device in response to the autofluorescence light produced by the tissue under examination;

illuminating the tissue under examination with a non-excitation light for a period which is shorter than a period for which the tissue is illuminated with the excitation light;

storing a second image created by the image sensing device in response to the non-illumination light that is reflected or scattered off the tissue under examination; and simultaneously displaying the first and second image on a monitor such that diseased tissue is delineated.

16. The method of claim 15, further comprising:

increasing a sensitivity of the image sensing device during the period when the tissue under examination is illuminated with the excitation light.

17. The method of claim 16, wherein the image sensing device is a CCD array and wherein the sensitivity of the CCD array is increased by binning pixels of the CCD array.

18. The method of claim 17, wherein the first and second images are simultaneously displayed by supplying the first image to a first color input of a color monitor and supplying the second image to a second color input of the color monitor.

19. An apparatus for producing images of tissue within a body, comprising:

a probe having a distal end to be inserted into the body near the tissue under examination and a proximal end to extend outside the body;

a light source at the proximal end of the probe for sequentially illuminating the tissue under examination with two or more bands of light over a timing cycle, one band of light being an excitation light that causes the tissue under examination to produce autofluorescence light having an intensity that differs for healthy and diseased tissue and the other band of light being non-excitation light, wherein the time for which the light source illuminates the tissue with the excitation light is greater than the time for which the light source illuminates the tissue with the non-excitation light;

an image sensor disposed at the distal end of the probe to produce an autofluorescence image of the tissue when illuminated with the excitation light and a reflectance image of the tissue when illuminated with the non-excitation light;

a filter disposed between the image sensor and the tissue under examination for filtering the excitation light from the light that reaches the image sensor and passing reflected or scattered non-excitation light;

an image storage device for storing the autofluorescence and reflectance images; and a display connected to receive the autofluorescence and reflectance images from the image storage device and for simultaneously displaying the autofluorescence and reflectance images of the tissue under examination to delineate diseased and normal tissue.

20. The apparatus of claim 19, further comprising a controller coupled to the image sensor for increasing a sensitivity of the image sensor during illumination of the tissue with the excitation light and decreasing the sensitivity of the image sensor during illumination of the tissue with the non-excitation light.

21. The apparatus of claim 19, wherein the timing cycle has a duration substantially equal to a duration of a video frame.

* * * * *

UNITED STATES PATENT AND TRADEMARK OFFICE
CERTIFICATE OF CORRECTION

PATENT NO. : 5,827,190
DATED : October 27, 1998
INVENTOR(S) : B. Palcic et al.

It is certified that error appears in the above-identified patent and that said Letters Patent is hereby corrected as shown below:

Column 12,
Line 7, "non-illumination" should read -- non-excitation --

Signed and Sealed this

Ninth Day of April, 2002

Attest:

Attesting Officer

JAMES E. ROGAN
Director of the United States Patent and Trademark Office